US009851287B2

(12) United States Patent
Hamann et al.

(10) Patent No.: US 9,851,287 B2
(45) Date of Patent: Dec. 26, 2017

(54) SIZE DISTRIBUTION DETERMINATION OF AEROSOLS USING HYPERSPECTRAL IMAGE TECHNOLOGY AND ANALYTICS

(71) Applicant: INTERNATIONAL BUSINESS MACHINES CORPORATION, Armonk, NY (US)

(72) Inventors: Hendrik F. Hamann, Yorktown Heights, NY (US); Levente Klein, Tuckahoe, NY (US); Alejandro G. Schrott, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 1 day.

(21) Appl. No.: 15/059,369

(22) Filed: Mar. 3, 2016

(65) Prior Publication Data

US 2017/0254734 A1 Sep. 7, 2017

(51) Int. Cl.
*G01N 15/02* (2006.01)
*G01J 3/28* (2006.01)
*G01N 21/27* (2006.01)

(52) U.S. Cl.
CPC ........ *G01N 15/0227* (2013.01); *G01J 3/2823* (2013.01); *G01N 21/27* (2013.01); *G01N 2015/0294* (2013.01); *G01N 2201/0612* (2013.01); *G01N 2201/12* (2013.01)

(58) Field of Classification Search
CPC ............... G01N 15/0227; G01N 21/27; G01N 2015/0294; G01N 2201/0612; G01N 2201/12; G01J 3/2823
USPC .................................................. 356/335–344
See application file for complete search history.

(56) References Cited

U.S. PATENT DOCUMENTS

| | | | |
|---|---|---|---|
| 7,046,859 B2 | 5/2006 | Bernstein et al. | |
| 8,502,975 B2 | 8/2013 | Roy et al. | |
| 2012/0212737 A1* | 8/2012 | Comstock, II | G01J 3/0218 356/326 |
| 2015/0235102 A1 | 8/2015 | Blagg | |
| 2016/0305820 A1* | 10/2016 | Zollars | G01N 15/1463 |
| 2017/0059408 A1* | 3/2017 | Korner | G01B 11/2536 |

FOREIGN PATENT DOCUMENTS

| | | |
|---|---|---|
| CN | 1556393 | 12/2004 |
| CN | 102750551 | 10/2012 |
| CN | 102507462 | 9/2013 |
| CN | 103714354 | 4/2014 |
| CN | 104279967 | 1/2015 |
| CN | 104483663 | 4/2015 |

(Continued)

*Primary Examiner* — Tri T Ton

(74) *Attorney, Agent, or Firm* — Tutunjian & Bitetto, P.C.; Vazken Alexanian

(57) ABSTRACT

An aerosol distribution determining system and method are provided. The system includes a set of light emitters for emitting electromagnetic radiation. The system further includes a hyperspectral imaging camera for capturing hyperspectral images of the electromagnetic radiation in an absence of and in a presence of an aerosol distribution. The system also includes a data processing system for determining at least one of a size, a vertical density distribution, and a shape of particles in the aerosol distribution based on a spectral response, an angular distribution, and a polarization of the aerosol distribution derived using the hyperspectral images.

19 Claims, 12 Drawing Sheets

(56) References Cited

FOREIGN PATENT DOCUMENTS

| | | |
|---|---|---|
| CN | 103398925 | 9/2015 |
| CN | 103616698 | 9/2015 |
| KR | 10-2010-0012377 | 2/2010 |

* cited by examiner

```
                    ┌─ Start ─┐                    ← 400
                    └────┬────┘
                         ▼
  ┌─────────────────────────────────────────────────────────┐
  │ Record spectral emission from a white laser diode in clear air. │ 405
  └─────────────────────────┬───────────────────────────────┘
                            ▼
  ┌─────────────────────────────────────────────────────────┐
  │ Record the spectral emission from a black disk in clean air │ 410
  └─────────────────────────┬───────────────────────────────┘
                            ▼
  ┌─────────────────────────────────────────────────────────┐
  │ Record the intensities of the emissions from the white laser diode │
  │ and the black disk in clean air and record the ratio of the        │ 415
  │ intensities of the emissions from the white laser diode and the    │
  │ black disk.                                                        │
  └─────────────────────────┬───────────────────────────────┘
                            ▼
  ┌─────────────────────────────────────────────────────────┐
  │ Create libraries of spectral response of the black disk to an      │
  │ aerosol distribution using particles having different well-defined │
  │ particle sizes and using different distribution densities, and record │
  │ the angular distribution of the recorded spectra for the narrow   │ 420
  │ aerosol distribution with the different well-defined particle sizes │
  │ and the different distribution densities. In an embodiment, step   │
  │ 420 is performed in a laboratory setting.                          │
  └─────────────────────────┬───────────────────────────────┘
                            ▼
  ┌─────────────────────────────────────────────────────────┐
  │ Sort the spectral response and angular distributions based on │ 425
  │ particle size.                                                │
  └─────────────────────────┬───────────────────────────────┘
                            ▼
  ┌─────────────────────────────────────────────────────────┐
  │ Identify polarization angles and emission angles for the particles │ 430
  │ having different well-defined particle sizes.                     │
  └─────────────────────────┬───────────────────────────────┘
                            ▼
                          ╱ A ╲
                          ╲___╱
```

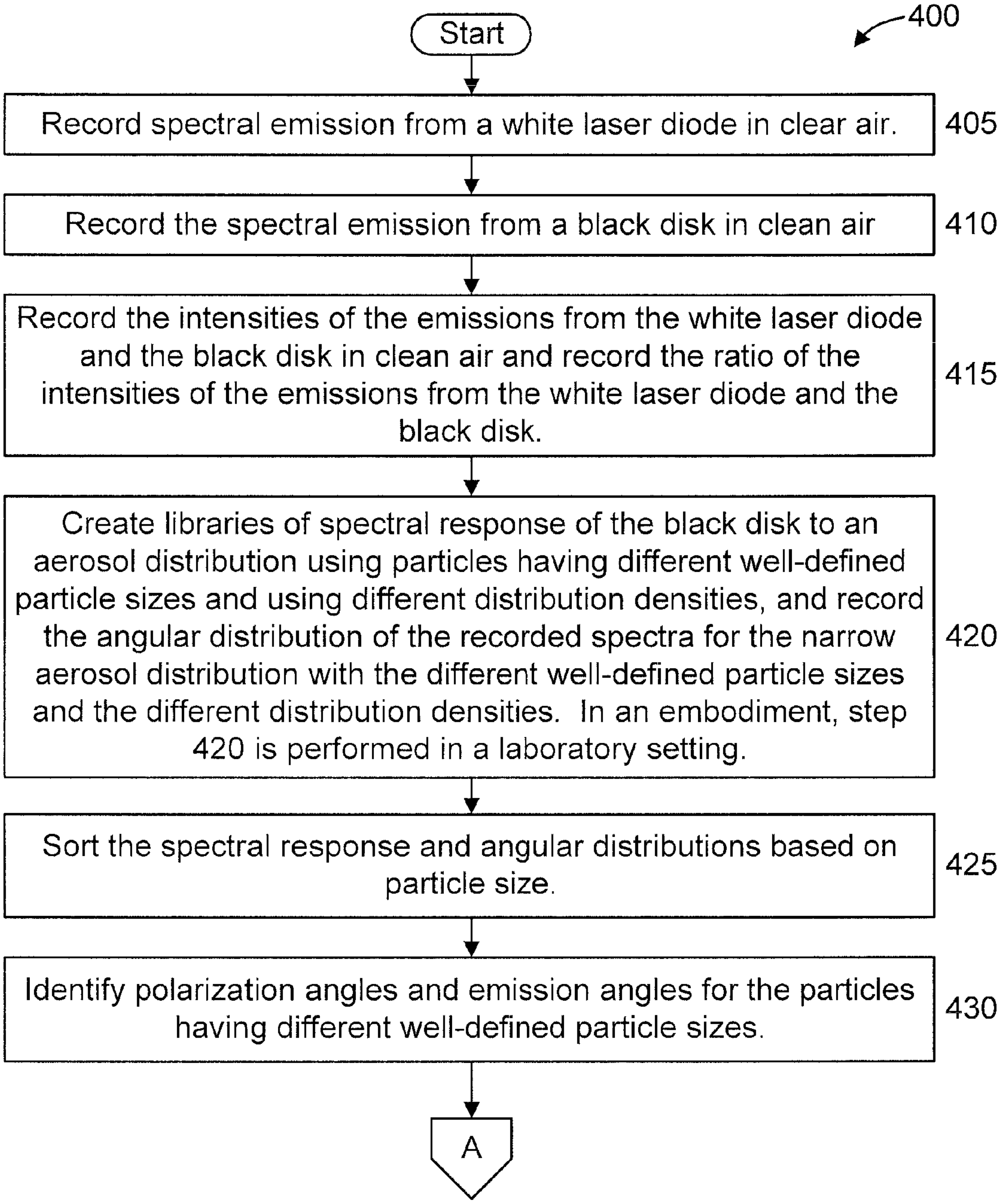

FIG. 4

SIZE DISTRIBUTION DETERMINATION OF AEROSOLS USING HYPERSPECTRAL IMAGE TECHNOLOGY AND ANALYTICS

BACKGROUND

Technical Field

The present invention relates generally to information processing and, in particular, to size distribution determination of aerosols using hyperspectral image technology and analytics.

Description of the Related Art

Fine particle pollution or PM2.5 describes particulate matter that is 2.5 micrometers in diameter and smaller. The increase of PM2.5 class particles in the atmosphere is a source of great concern and has triggered government programs directed to obtaining more reliable measurements of such particles in order to generate better emission control methods.

Current detection methods for PM2.5 include the use of satellite imaging. In particular, satellite imaging has been used to determine source distribution and evolution of aerosols. However, satellite data has elements that are dependent on soil reflectivity and atmospheric conditions and thus require extensive analyses. Furthermore, for some determinations, the geographical reach and spatial resolution provided by satellite data acquisition is not sufficient to provide adequate detection of PM2.5.

For example, PM2.5 distribution detection for certain applications such as at the urban center level require PM2.5 distribution detection at the street or neighborhood level. Satellites acquire reflections in a very large column of atmosphere where lower and higher levels of the atmosphere contribute to the reflection. Extracting information and localizing particle distribution as function of height is challenging. In many cases, a fusion of data provided from a satellite and calibrated at the local level is required.

The use of satellites for PM2.5 distribution detection is a continuously evolving technology due to improvements in image detection techniques. The spatial resolution of such detection is on the kilometer scale and data is acquired every day or sparser. However, for some determinations of geographical reach, the resolution provided by satellite data acquisition is not sufficient. This is typically the case in large urban areas or industrial locations where dust variations across a few kilometers can be significant and can be affected by buildings, streets, and so forth. Moreover, the particle distributions in such scenarios are strongly correlated with traffic patterns and/or construction sites.

Thus, there is a need for improved size distribution determination of aerosols involving PM2.5.

SUMMARY

According to an aspect of the present principles, an aerosol distribution determining system is provided. The system includes a set of light emitters for emitting electromagnetic radiation. The system further includes a hyperspectral imaging camera for capturing hyperspectral images of the electromagnetic radiation in an absence of and in a presence of an aerosol distribution. The system also includes a data processing system for determining at least one of a size, a vertical density distribution, and a shape of particles in the aerosol distribution based on a spectral response, an angular distribution, and a polarization of the aerosol distribution derived using the hyperspectral images.

According to another aspect of the present principles, a method for aerosol distribution determination is provided. The method includes emitting, by a set of light emitters, electromagnetic radiation. The method further includes capturing, by a hyperspectral imaging camera, hyperspectral images of the electromagnetic radiation in an absence of and in a presence of an aerosol distribution. The method also includes determining, by a data processing system, at least one of a size, a vertical density distribution, and a shape of particles in the aerosol distribution based on a spectral response, an angular distribution, and a polarization of the aerosol distribution derived using the hyperspectral images.

According to yet another aspect of the present principles, a computer program product for aerosol distribution determination is provided. The computer program product includes a non-transitory computer readable storage medium having program instructions embodied therewith. The program instructions are executable by a computer to cause the computer to perform a method. The method includes emitting, by a set of light emitters, electromagnetic radiation. The method further includes capturing, by a hyperspectral imaging camera, hyperspectral images of the electromagnetic radiation in an absence of and in a presence of an aerosol distribution. The method also includes determining, by a data processing system, at least one of a size, a vertical density distribution, and a shape of particles in the aerosol distribution based on a spectral response, an angular distribution, and a polarization of the aerosol distribution derived using the hyperspectral images.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIGS. 4-6 show an exemplary method 400 for determining the size of a distribution of aerosols using white laser diodes, in accordance with an embodiment of the present principles;

DETAILED DESCRIPTION OF PREFERRED EMBODIMENTS

Figure 1:
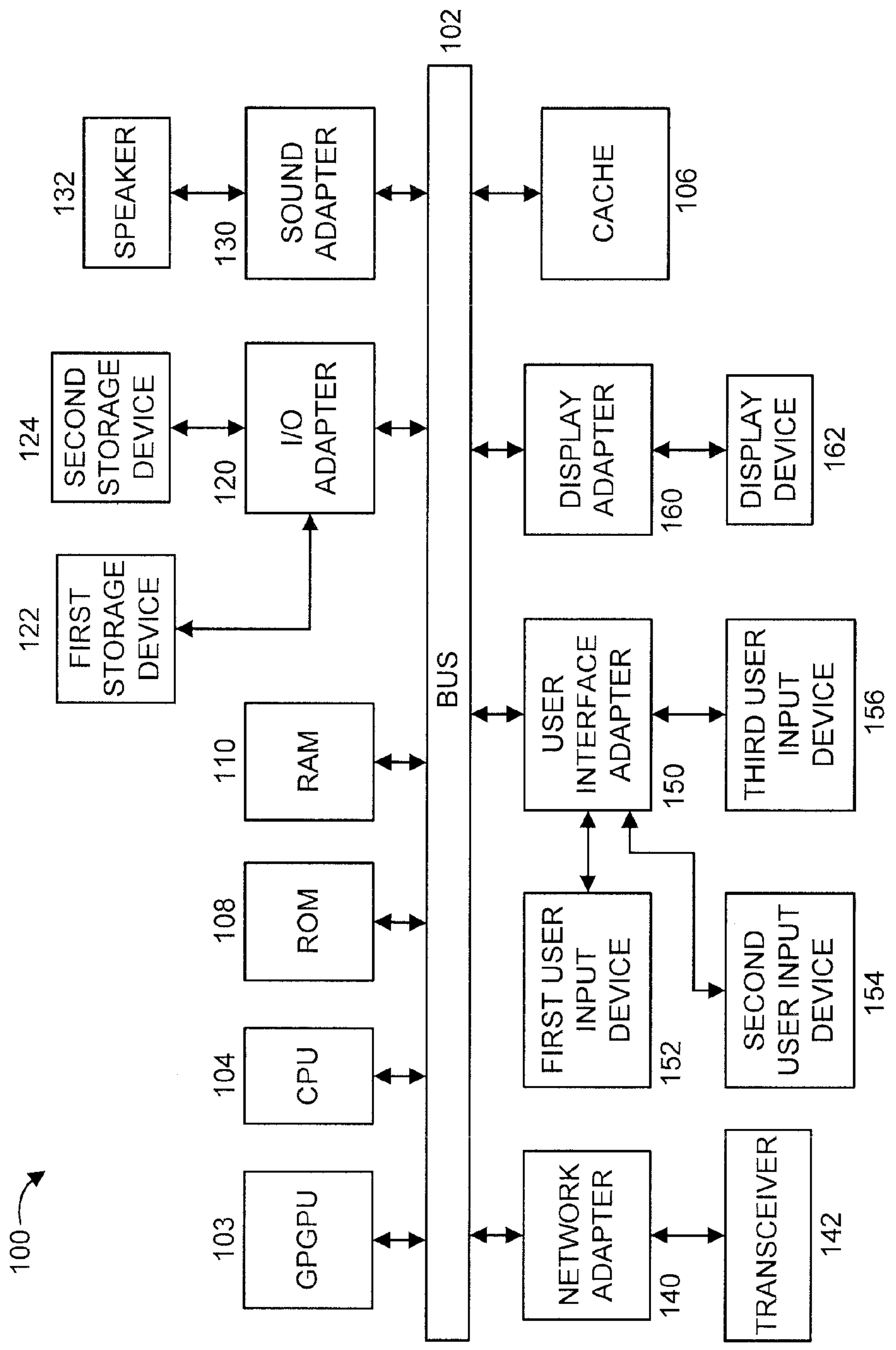
FIG. 1 shows an exemplary processing system 100 to which the present principles may be applied, in accordance with an embodiment of the present principles.

The present principles are directed to size distribution determination of aerosols using hyperspectral image (HIS) technology and analytics.

In an embodiment, the present principles utilize hyperspectral imaging technology for the local determination of aerosol distribution within the PM2.5 classification. In an embodiment, the present principles use one or more static emission points that are distributed on the ground and a mobile or stationary camera(s).

In an embodiment, the present principles provide a way to determine the size of a distribution of aerosols by observing the MIE scatting from a collimated light source using hyperspectral imaging.

In an embodiment, the present principles can exploit the road map capability of hyperspectral imaging, which makes it possible to create a very complex hyperspectral cube using light weight, low power, and fast snapshot cameras. Images from laser diodes and their halo are taken by hyperspectral cameras mounted on various vehicles/objects. A laser diode array is distributed in height by attachment to poles or to panels being suspended by a device capable of flight. The laser diode array can also be distributed on the ground for column assessment from a plane, helicopter, drone, and so forth.

The present principles described here allow a high density measurements across a distribution of locations where diodes and blackbody disks can be positioned on buildings, cell towers, hospitals, schools, and other places/objects with well knows geospatial locations. Using a mobile detector, a large number of sensors can be covered in a short period of time by programming the data collection vehicles (e.g., planes, helicopters, drones, and so forth) to travel on a well-defined path. The present principles can detect aerosols, dust, pollution plumes, chemicals (such as, e.g., but not limited to, methane, CO2, and so forth), and so forth. The detection range is dependent upon the data collection vehicle/object. In an embodiment, the collection range can be in hundreds of feet, corresponding to the height of drone flying. It is to be noted that pollution at such height is affecting population health and the densest distribution is likely to be found in this range.

In an embodiment, the spectral response, angular distribution, and the polarization are used to extract information about particle size, vertical density distribution and shape of particles. The signal is also verified against a library of well-known spectra that are obtained in a laboratory using calibrated instruments that are not usually portable. The laboratory data set is used to increase the confidence in acquired data from a discrete number of wavelengths and to assign the correct particulates in size, density and chemical composition.

In an embodiment, once a calibration of a point is obtained outside (where we have a well-defined wavelength diode), the identified particle size and composition can be extrapolated to the surroundings. This would be similar to, for example, a large image where one or multiple points serve as a calibration point and all other points will be assigned a similar distribution but the variation of the signal will be attributed to spatial variation in density.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
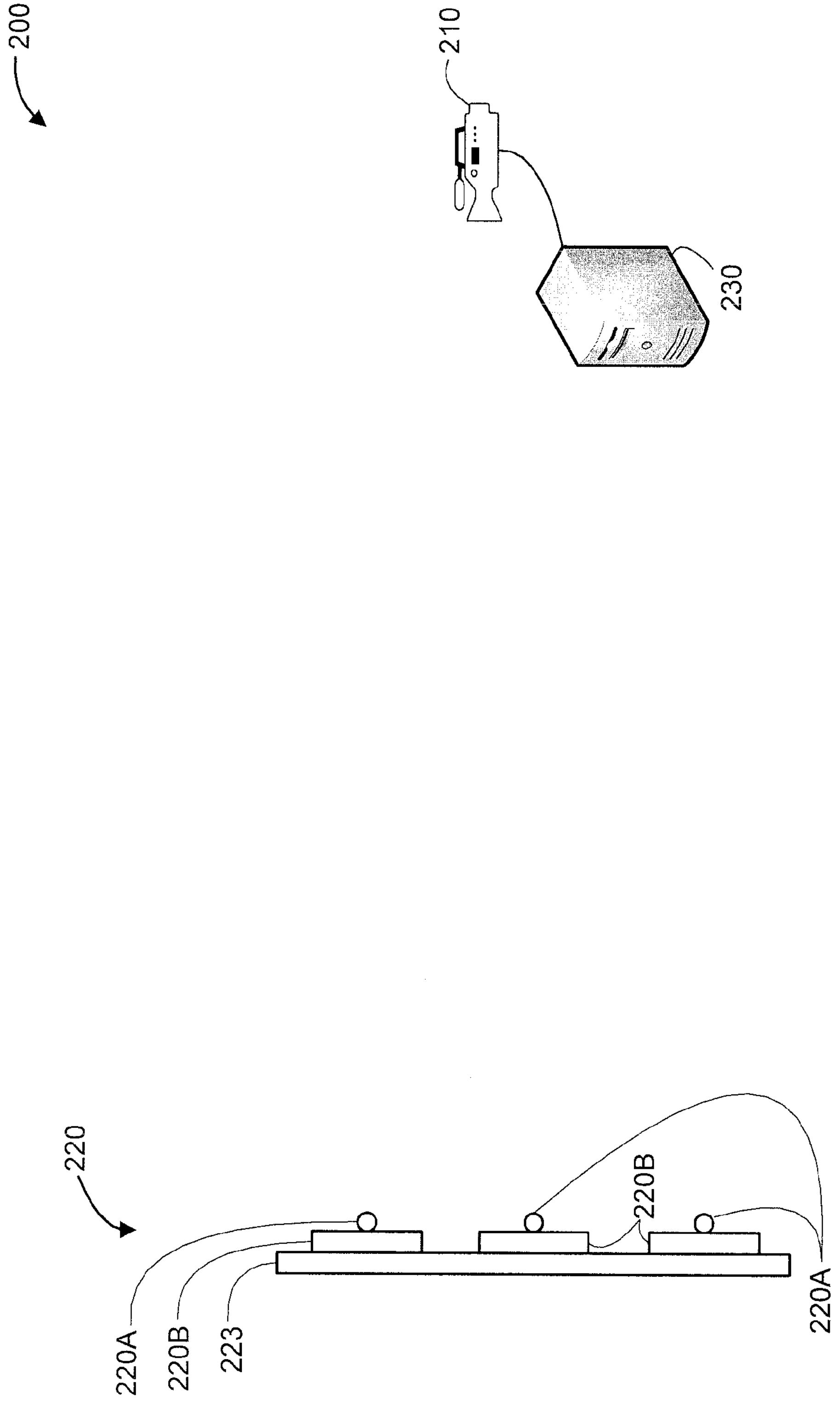
FIG. 2 shows an exemplary system 200 for determining the size of a distribution of aerosols.

Moreover, it is to be appreciated that system 200 described below with respect to FIG. 2 is a system for implementing respective embodiments of the present principles. Part or all of processing system 100 may be implemented in one or more of the elements of system 200.

Figure 5:
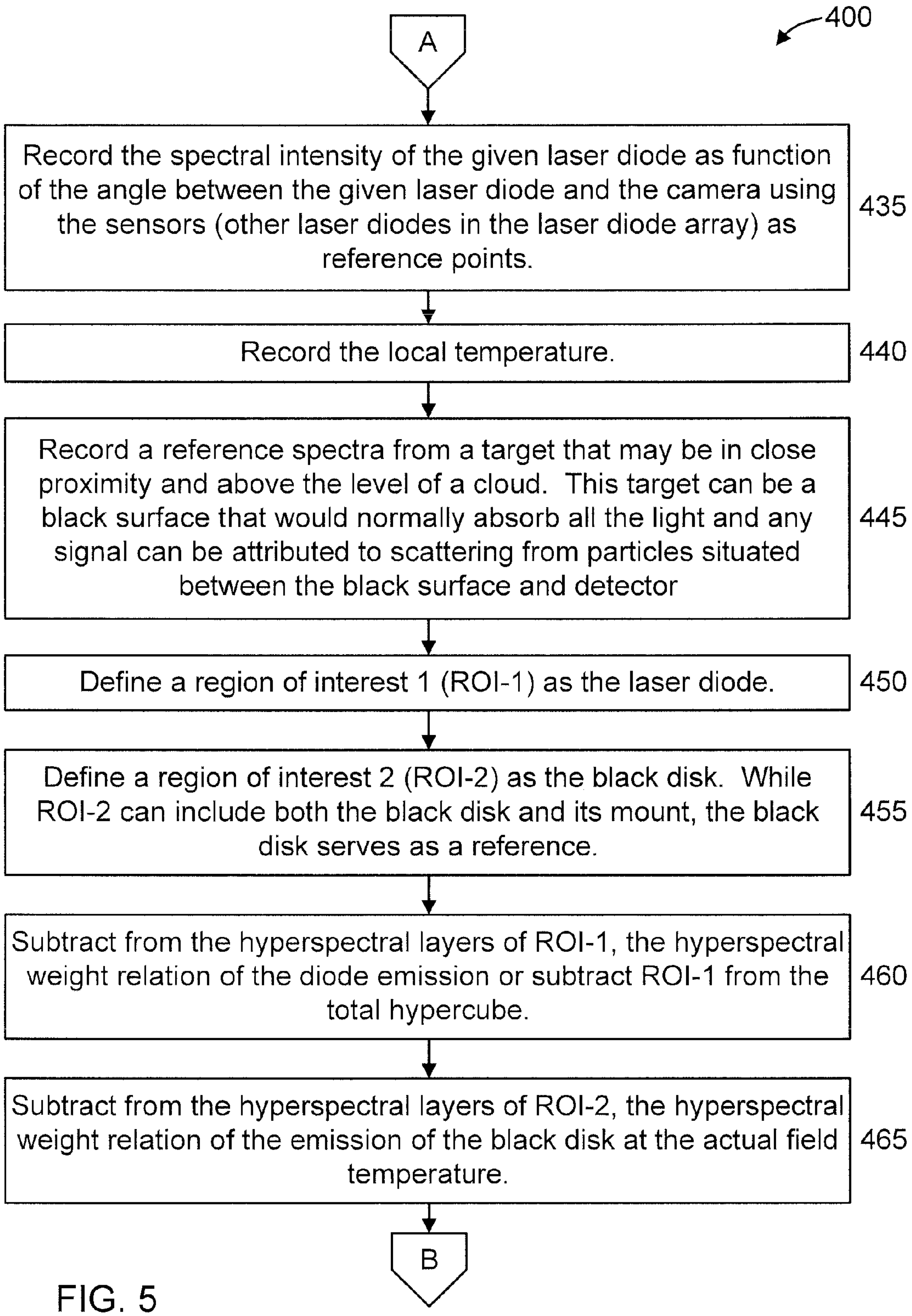
Figure 6:
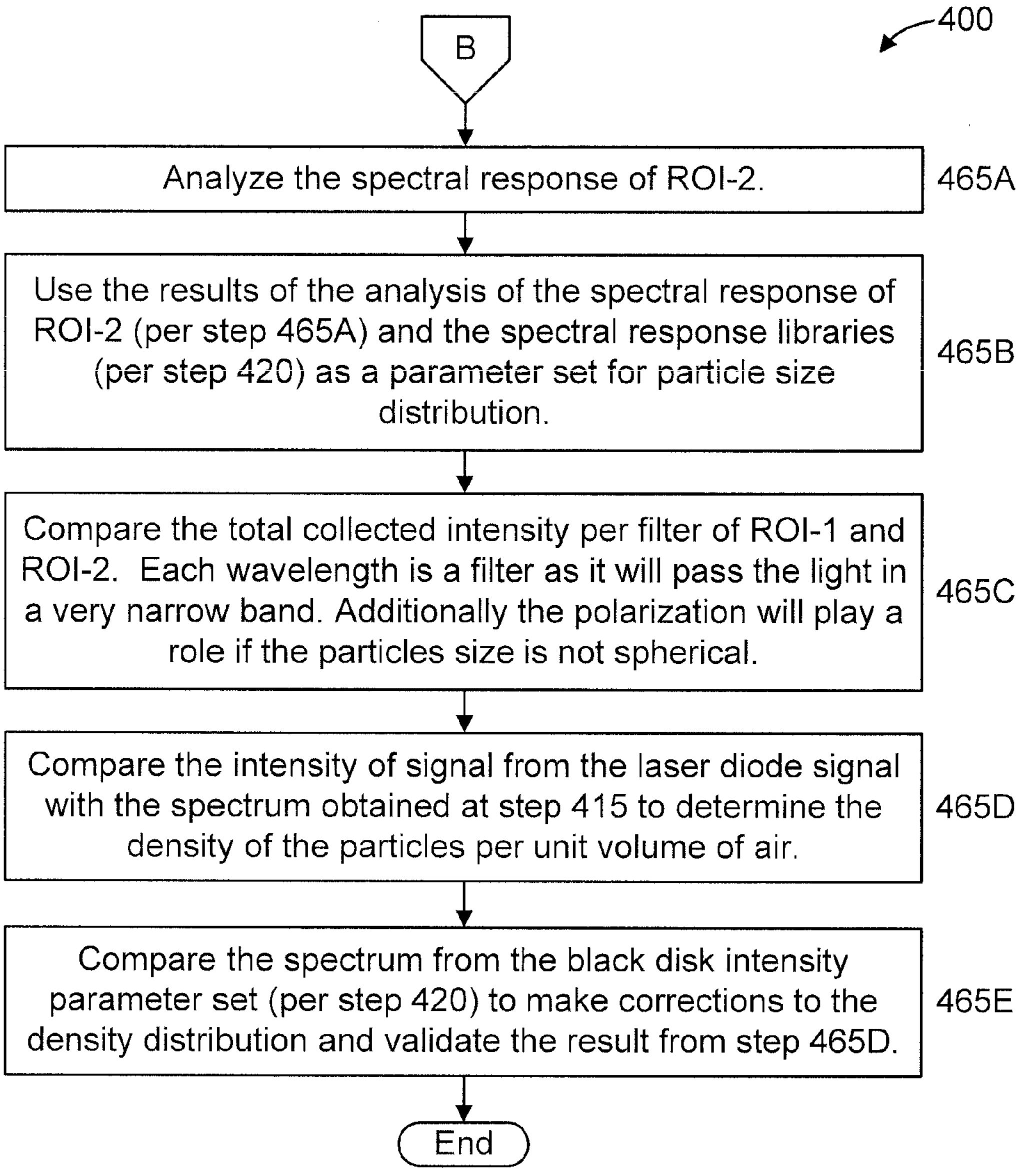
Figure 7:
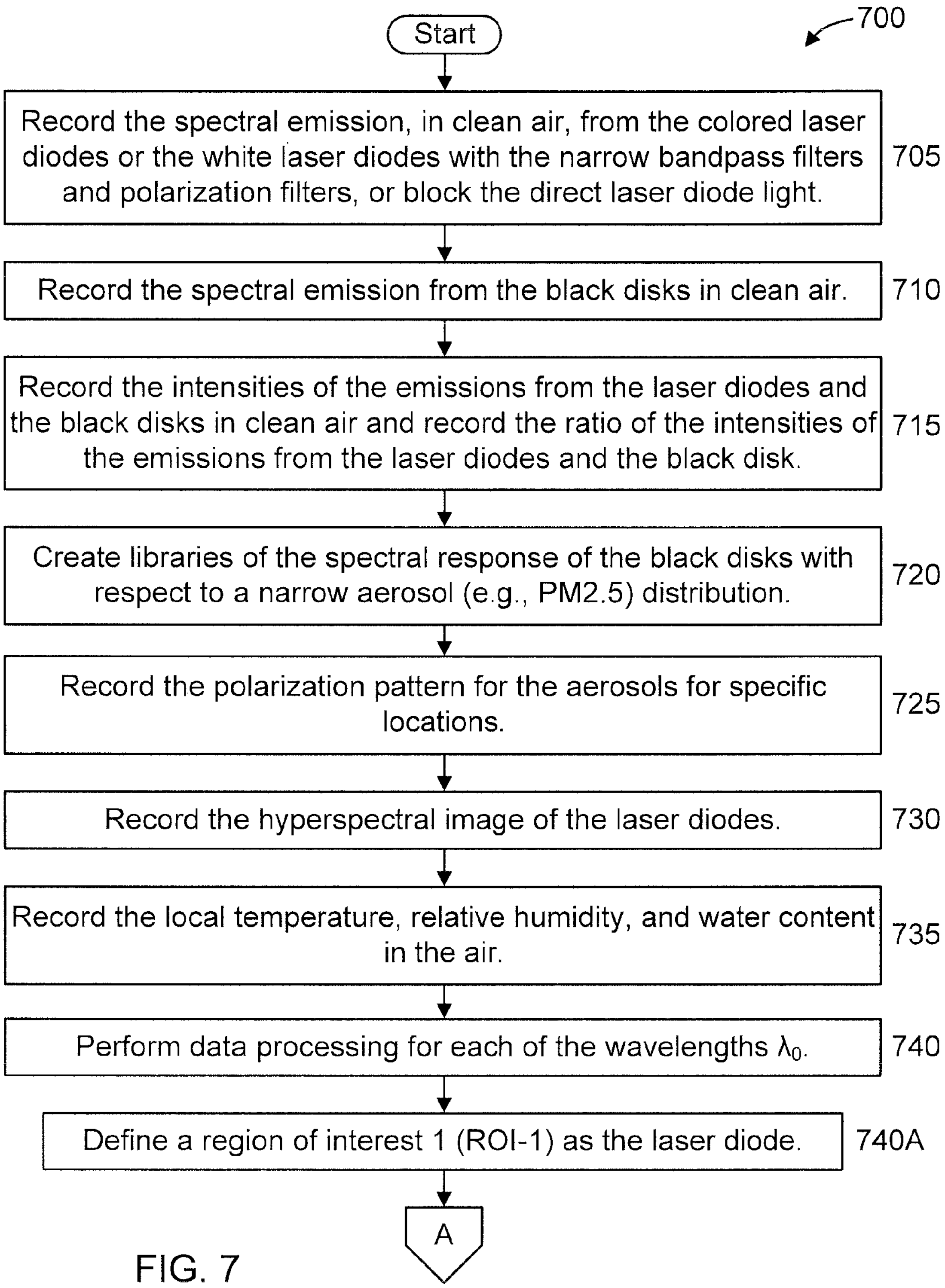
FIGS. 7-9 shows an exemplary method 700 for determining the size of a distribution of aerosols using colored laser diodes or white laser diodes with narrow bandpass filters and polarization filters in front of the white laser diodes, in accordance with an embodiment of the present principles.
Figure 8:
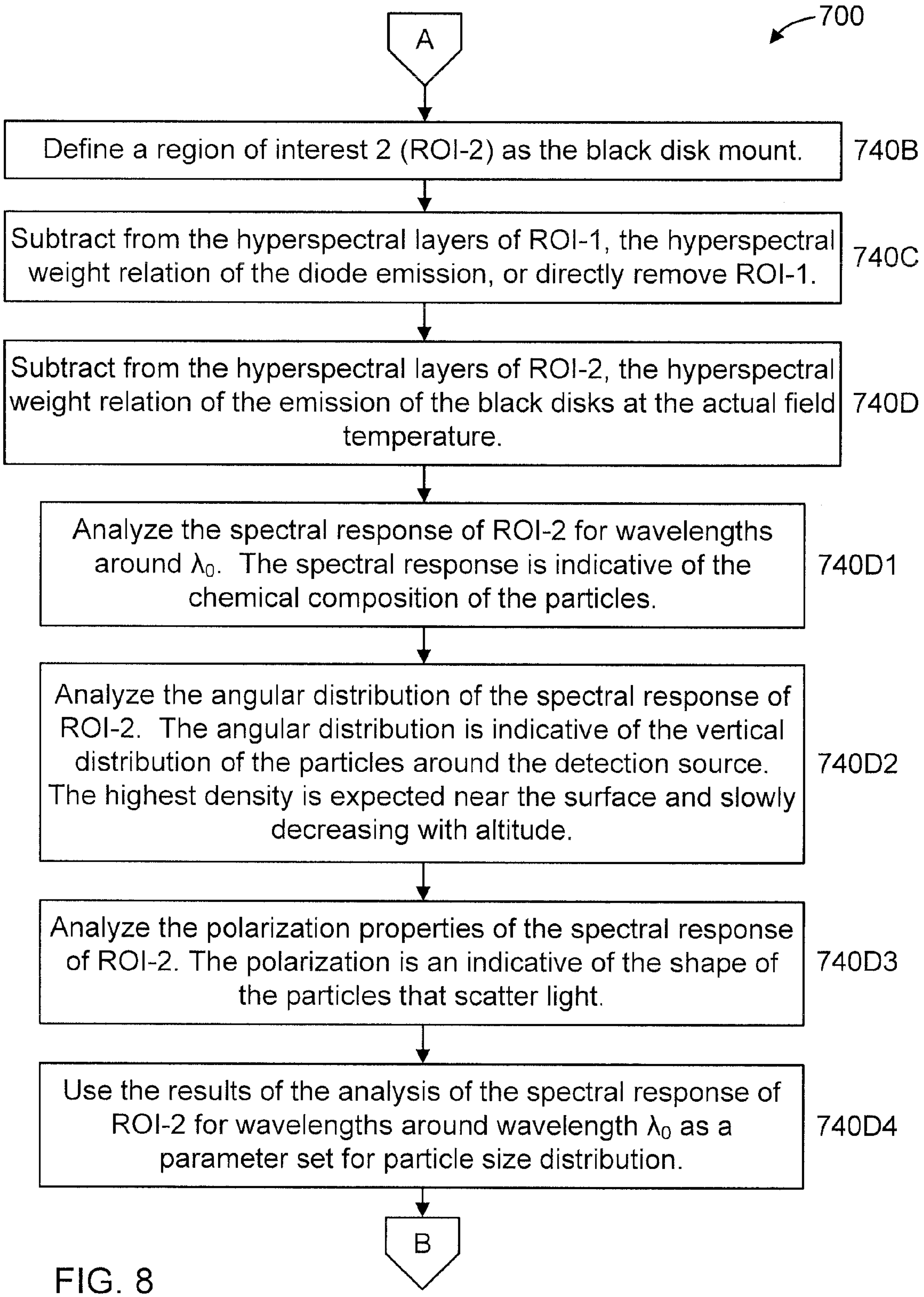
Figure 9:
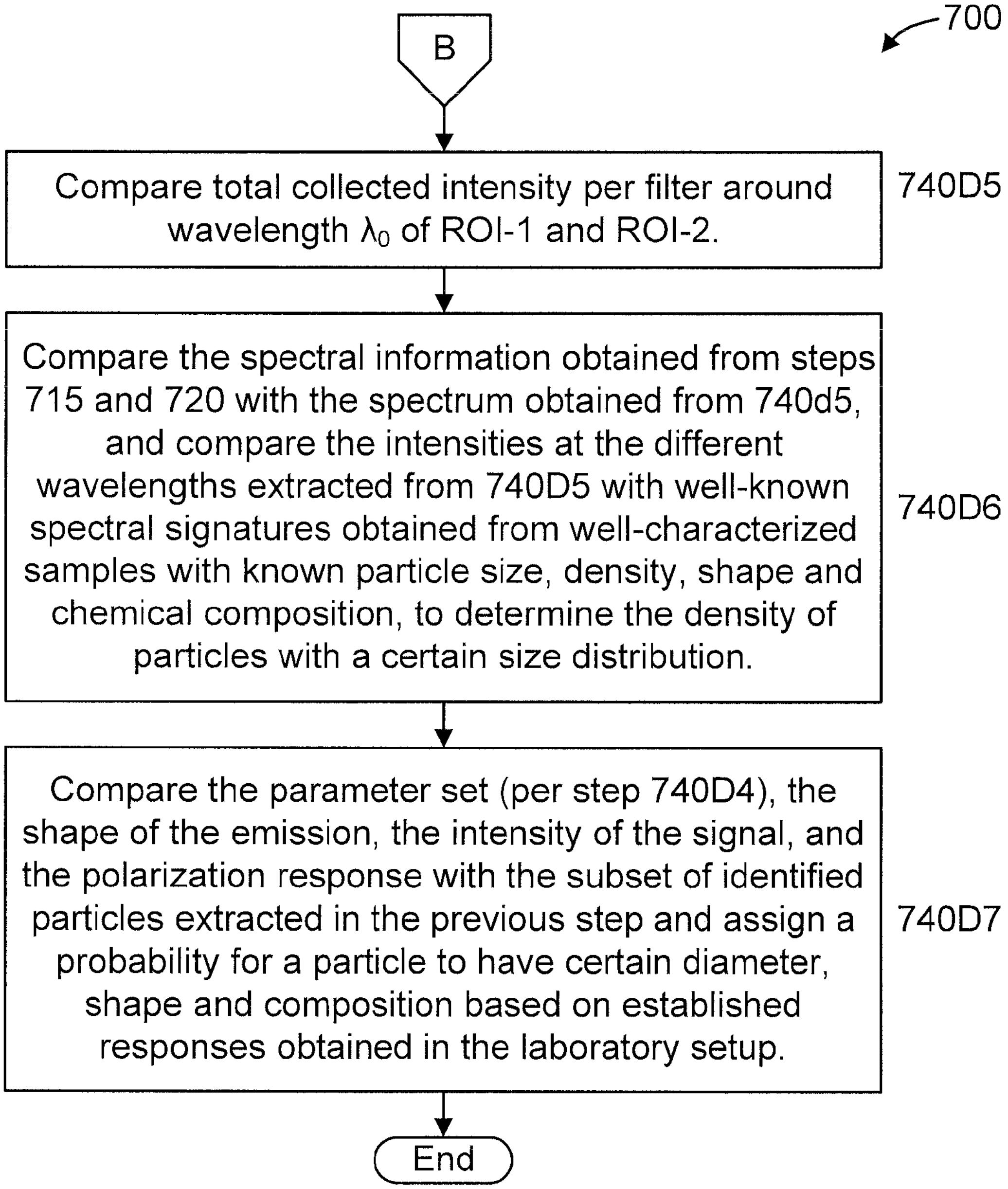

Further, it is to be appreciated that processing system 100 may perform at least part of the method described herein including, for example, at least part of method 400 of FIGS. 4-6 and/or at least part of method 700 of FIGS. 7-9. Similarly, part or all of system 200 may be used to perform at least part of method 400 of FIGS. 4-6 and/or at least part of method 700 of FIGS. 7-9.

FIG. 2 shows an exemplary system 200 for determining the size of a distribution of aerosols, in accordance with an embodiment of the present principles.

The system 200 includes a hyperspectral imaging (HIS) camera 210 (also interchangeably referred to as a "hyperspectral camera" in short), a laser diode (or other electromagnetic radiation source) array 220, and a data processing system 230. For the sake of brevity and illustration, the following description will involve laser diodes, noting that the same can be replaced by other sources of electromagnetic radiation including, but not limited to, Tungsten lamps and/or other calibrated (known spectral emission) light emitters. As such, it is to be appreciated that these various sources of electromagnetic radiation are interchangeably and generally referred to herein as light emitters.

Figure 3:
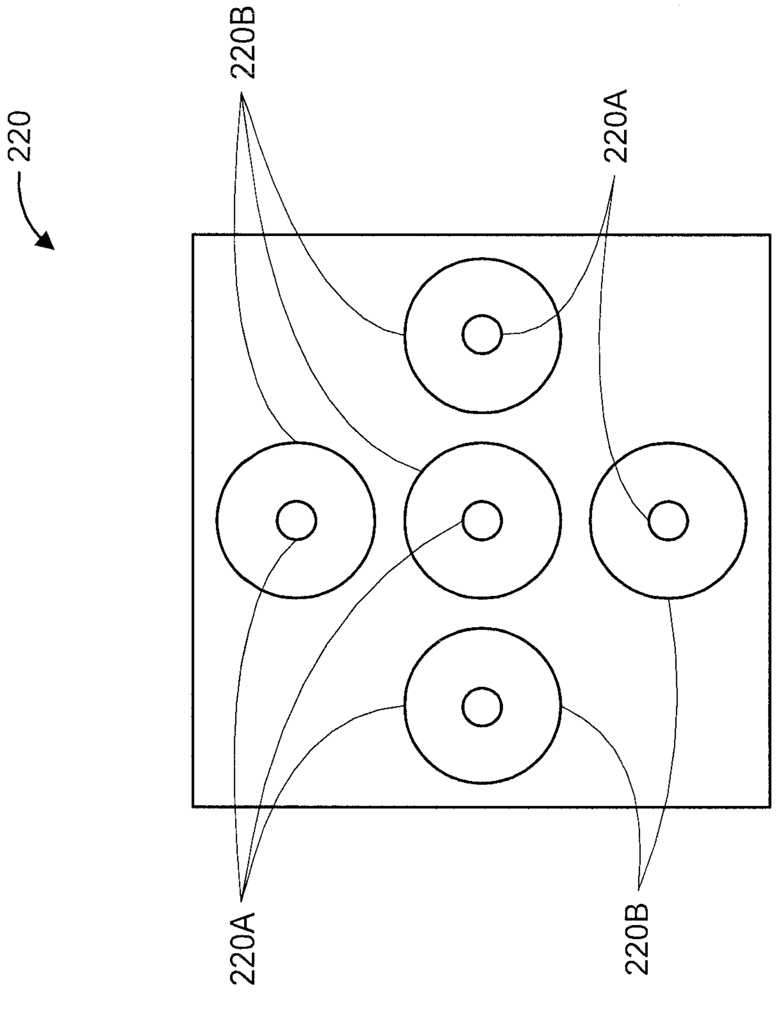
FIG. 3 shows a top view of the laser diode array 220 of FIG. 2, in accordance with an embodiment of the present principles.

FIG. 3 shows a top view of the laser diode array 220 of FIG. 2, in accordance with an embodiment of the present principles. It is to be appreciated that any spacing can be used between the elements of the diode array, depending upon the implementation. Similarly, any number of elements of the diode array can be used, depending upon the implementation.

In the embodiments of FIGS. 2 and 3, the laser diode array 220 includes a set of laser diodes (collectively and individually denoted by the reference characters "220A") and a set of black disks (collectively and individually denoted by the reference characters "220W"). In the embodiments of FIGS. 2 and 3, each of the black disks 220A in the array is mounted on a backing material 223 (here, a backing board, although any suitable material (e.g., wood, plastic, metal, and so forth) in any form/shape (e.g., pole, and so forth) can be used, including existing structure or infrastructure found in a location at which the present principles are to be deployed). Each of the laser diodes 220A is each mounted and/or otherwise disposed on a respective one of the black disks 220B. The pairs formed from each laser diode 220A being mounted on a corresponding black disk 220B can be mounted at any angle relative to the earth. For example, the flat surface of the black disk 220B in a formed pair can be mounted parallel relative to the earth, perpendicular relative to the earth, and so forth. The pairs and/or array can be mounted on, but is not limited to, for example, a tower, building, pole, and so forth. The black disks 220B are physical objects that ideally absorb all incident electromagnetic radiation, regardless of frequency or angle of incidence. Hence, as used herein, the term "black disk" refers to a physical disk having at least an externally black body for absorbing incident electromagnetic radiation.

The hyperspectral camera 210 can collect information as a set of "images", where each image represents a narrow wavelength range of the electromagnetic spectrum. These "images" are then combined, by the data processing system 230, to form a three-dimensional (x,y,λ) hyperspectral data cube for processing and analysis, where x and y represent two spatial dimensions of the scene, and λ represents the spectral dimension (comprising a range of wavelengths). The hyperspectral data cube can be formed using any of the following data acquisition techniques: spatial scanning; spectral scanning; non-scanning (snapshot); and spatio-spectral scanning.

The hyperspectral camera 210 can be mobile or stationary, depending on the implementation. For example, regarding the former, the hyperspectral camera 210 can be mounted on a plane, helicopter, drone, and so forth. In such a case, the hyperspectral camera 210 can obtain angular recordings of the diodes spectra.

Moreover, regarding the latter, the (or another) hyperspectral camera 210 can be alternatively or supplementary mounted on, for example, a very tall building (e.g., a skyscraper), and so forth.

The hyperspectral image of the laser diode array 220 can be used to assess the extinction of the laser diode light at different angles and/or at different wavelengths. Moreover, the hyperspectral image of the laser diode array 220 can be used to assess the halo around the laser diodes in the laser diode array 220 due to scattering, which can involve selecting pixels from the black disk and/or screening the laser diodes.

The data processing system 230 performs data processing of results from data collection using the hyperspectral camera 210.

While the embodiment of FIG. 2 shows a single hyperspectral camera, a single laser diode array and a single data processing system 230, in other embodiments, more than one of any of the preceding elements can be employed, while maintaining the spirit of the present principles. In addition, a well calibrated light source, such as tungsten lamp could be used.

In an embodiment, the present principles can take into account the physical properties of light scattering by particles (Mie scattering) and how their absorption affects the intensity of light detected at different wave lengths.

In an embodiment, the present principles use the laser diode array 220 in the field, where hyperspectral images of the laser diodes and the close surrounding (halo) generated by the diodes are obtained by the hyperspectral camera 210. During a data collection phase, the hyperspectral camera 210 is located at an appropriate distance to determine the particle size distribution of the aerosol cloud via appropriate analytics.

A brief description will now be given regarding some of the parameters governing scattering, to which the present principles can be applied, according to an embodiment of the present principles.

(1) The wavelength (λ) of the incident radiation.

(2) The size of the scattering particle, usually expressed as the non-dimensional size parameter x, as follows:

$$x=(2\pi r)/\lambda,$$

where r denotes the radius of a spherical particle, and λ denotes wavelength.

(3) The particle optical properties relative to the surrounding medium: the complex refractive index.

For MIE scattering on particles where the diameter of particles is comparable to the detection wavelength, x~1.

A brief description will now be given regarding MIE scattering, to which the present principles can be applied, in accordance with an embodiment of the present principles.

MIE theory describes the scattering and absorption of electromagnetic radiation by spherical or non-spherical particles though solving Maxwell equations. MIE theory operates on the following assumptions: (1) the particle size is comparable to the detection wavelength; and (2) the particle is homogeneous (therefore, it is characterized by a single refractive index at a given wavelength).

It is to be appreciated that while the figures provided herein show one or more laser diodes being used as a source of electromagnetic radiation, the present principles are not limited to the same and, thus, other sources of electromagnetic radiation can also be used. For example, other types of electromagnetic sources to which the present principles can be applied include, but are not limited to, Tungsten lamps and so forth.

FIGS. 4-6 show an exemplary method 400 for determining the size of a distribution of aerosols using white laser diodes mounted on black disks, in accordance with an embodiment of the present principles. While the example of FIGS. 4-6 is described with respect to a single white laser diode on a single black disk for the sake of brevity and illustration, the method of FIGS. 4-6 can be readily applied to a diode array that includes more than one pair formed from a white laser diode and a black disk as described herein and shown in at least FIGS. 2 and 3, as readily appreciated by one of ordinary skill in the art, while maintaining the spirit of the present principles. Moreover, as noted above, in an embodiment, a Tungsten lamp or other light emitter can be used in place of the laser diode. However, for the sake of illustration and clarity, the example of FIGS. 4-6 are described with respect to a laser diode.

In the embodiment of FIGS. 4-6, steps 405 through 430 are performed in a laboratory or similarly appropriate setting, while steps 435 through 450 are performed in the field, as readily appreciated by one of ordinary skill in the art. Steps 455 through 470 can be performed in any of the preceding settings. Of course, the steps of method 400 are not limited to the preceding settings and can be performed in other settings while maintaining the spirit of the present principles.

At step 405, record spectral emission from a white laser diode in clear air.

At step 410, record the spectral emission from a black disk in clean air.

At step 415, record the intensities of the emissions from the white laser diode and the black disk in clean air and record the ratio of the intensities of the emissions from the white laser diode and the black disk.

At step 420, create libraries of spectral response of the black disk to an aerosol distribution using particles having different well-defined particle sizes and using different distribution densities, and record the angular distribution of the recorded spectra for the narrow aerosol distribution with the different well-defined particle sizes and the different distribution densities. In an embodiment, step 420 is performed in a laboratory setting.

At step 425, sort the spectral response and angular distributions based on particle size.

At step 430, identify polarization angles and emission angles for the particles having different well-defined particle sizes.

At step 435, record the spectral intensity of the given laser diode as function of the angle between the given laser diode and the camera using the sensors (other laser diodes in the laser diode array) as reference points.

At step 440, record the local temperature.

At step 445, record a reference spectra from a target that may be in close proximity and above the level of a cloud. This target can be a black surface that would normally absorb all the light and any signal can be attributed to scattering from particles situated between the black surface and detector.

At step 450, define a region of interest 1 (ROI-1) as the laser diode.

At step 455, define a region of interest 2 (ROI-2) as the black disk. While ROI-2 can include both the black disk and its mount, the black disk serves as a reference.

At step 460, subtract from the hyperspectral layers of ROI-1, the hyperspectral weight relation of the diode emission or subtract ROI-1 from the total hypercube. The system response will have a wavelength dependence as the scattering at different wavelengths will change. The change will be dependent on the size of particles and their chemical composition. The method will acquire the response for multiple wavelength diodes and subtract the black surface signal to create multiple data points that will approximate the spectral response. Each wavelength will be one layer in the hypercube that includes individual layers at different wavelength. The gap between the data points can be fitted using polynomial curves to create a continuous spectral response. The spectral response can be compared with a continuous measurement of particles of different sizes and chemical properties obtained in the laboratory using a spectrometer.

At step 465, subtract from the hyperspectral layers of ROI-2, the hyperspectral weight relation of the emission of the black disk at the actual field temperature.

In an embodiment, step 465 includes steps 465A through 465E.

At step 465A, analyze the spectral response of ROI-2.

At step 465B, use the results of the analysis of the spectral response of ROI-2 (per step 465A) and the spectral response libraries (per step 420) as a parameter set for particle size distribution.

At step 465C, compare the total collected intensity per filter of ROI-1 and ROI-2. Each wavelength is a filter as it will pass the light in a very narrow band. Additionally the polarization will play a role if the particles size is not spherical.

At step 465D, compare the intensity of signal from the laser diode signal with the spectrum obtained at step 415 to determine the density of the particles per unit volume of air.

At step 465, compare the spectrum from the black disk intensity parameter set (per step 420) to make corrections to the density distribution and validate the result from step 465D.

FIGS. 7-9 show an exemplary method 700 for determining the size of a distribution of aerosols using colored laser diodes or white laser diodes with narrow bandpass filters and polarization filters in front of the white laser diodes, in accordance with an embodiment of the present principles. The laser diodes and filters are mounted on black disks.

It is to be appreciated that the use of color laser diodes or white laser diodes with narrow bandpass filters and polarization filters in front of the white laser diodes can provide more precision in the infrared region of the electromagnetic spectrum. In the embodiment of FIGS. 7-9, the laser diodes have different wavelengths $\lambda_0$ defined approximately by $x=2\pi a/\lambda_0$, where a denotes the approximate radius of the particles.

In the embodiment of FIGS. 7-9, steps 705 through 720 are performed in a laboratory or similarly appropriate setting, while steps 725 through 735 are performed in the field, as readily appreciated by one of ordinary skill in the art. Step 740 can be performed in any of the preceding settings. Of course, the steps of method 600 are not limited to the preceding settings and can be performed in other settings while maintaining the spirit of the present principles.

At step 705, record the spectral emission, in clean air, from the colored laser diodes or the white laser diodes with the narrow bandpass filters and polarization filters, or block the direct laser diode light.

At step 710, record the spectral emission from the black disks in clean air.

At step 715, record the intensities of the emissions from the laser diodes and the black disks in clean air and record the ratio of the intensities of the emissions from the laser diodes and the black disk.

At step 720, create libraries of the spectral response of the black disks with respect to a narrow aerosol (e.g., PM2.5) distribution.

At step 725, record the polarization pattern for the aerosols for specific locations.

At step 730, record the hyperspectral image of the laser diodes.

At step 735, record the local temperature, relative humidity, and water content in the air.

At step 740, perform data processing for each of the wavelengths $\lambda_0$. In an embodiment, step 740 includes steps 740A through 740D.

At step 740A, define a region of interest 1 (ROI-1) as the laser diode.

At step 740B, define a region of interest 2 (ROI-2) as the black disk mount.

At step 740C, subtract from the hyperspectral layers of ROI-1, the hyperspectral weight relation of the diode emission, or directly remove ROI-1.

At step 740D, subtract from the hyperspectral layers of ROI-2, the hyperspectral weight relation of the emission of the black disks at the actual field temperature.

In an embodiment, step 740D includes steps 740D1 through 740D7.

At step 740D1, analyze the spectral response of ROI-2 for wavelengths around $\lambda_0$. The spectral response is indicative of the chemical composition of the particles.

At step 740D2, analyze the angular distribution of the spectral response of ROI-2. The angular distribution is indicative of the vertical distribution of the particles around the detection source. The highest density is expected near the surface and slowly decreasing with altitude.

At step 740D3, analyze the polarization properties of the spectral response of ROI-2. The polarization is an indicative of the shape of the particles that scatter light.

At step 740D4, use the results of the analysis of the spectral response of ROI-2 for wavelengths around wavelength $\lambda_0$ as a parameter set for particle size distribution.

At step 740D5, compare total collected intensity per filter around wavelength Xo of ROI-1 and ROI-2.

At step 740D6, compare the spectral information obtained from steps 715 and 720 with the spectrum obtained from 740*d*5, and compare the intensities at the different wavelengths extracted from 740D5 with well-known spectral signatures obtained from well-characterized samples with known particle size, density, shape and chemical composition, to determine the density of particles with a certain size distribution.

At step 740D7, compare the parameter set (per step 740D4), the shape of the emission, the intensity of the signal, and the polarization response with the subset of identified particles extracted in the previous step and assign a probability for a particle to have certain diameter, shape and composition based on established responses obtained in the laboratory setup.

Figure 10:
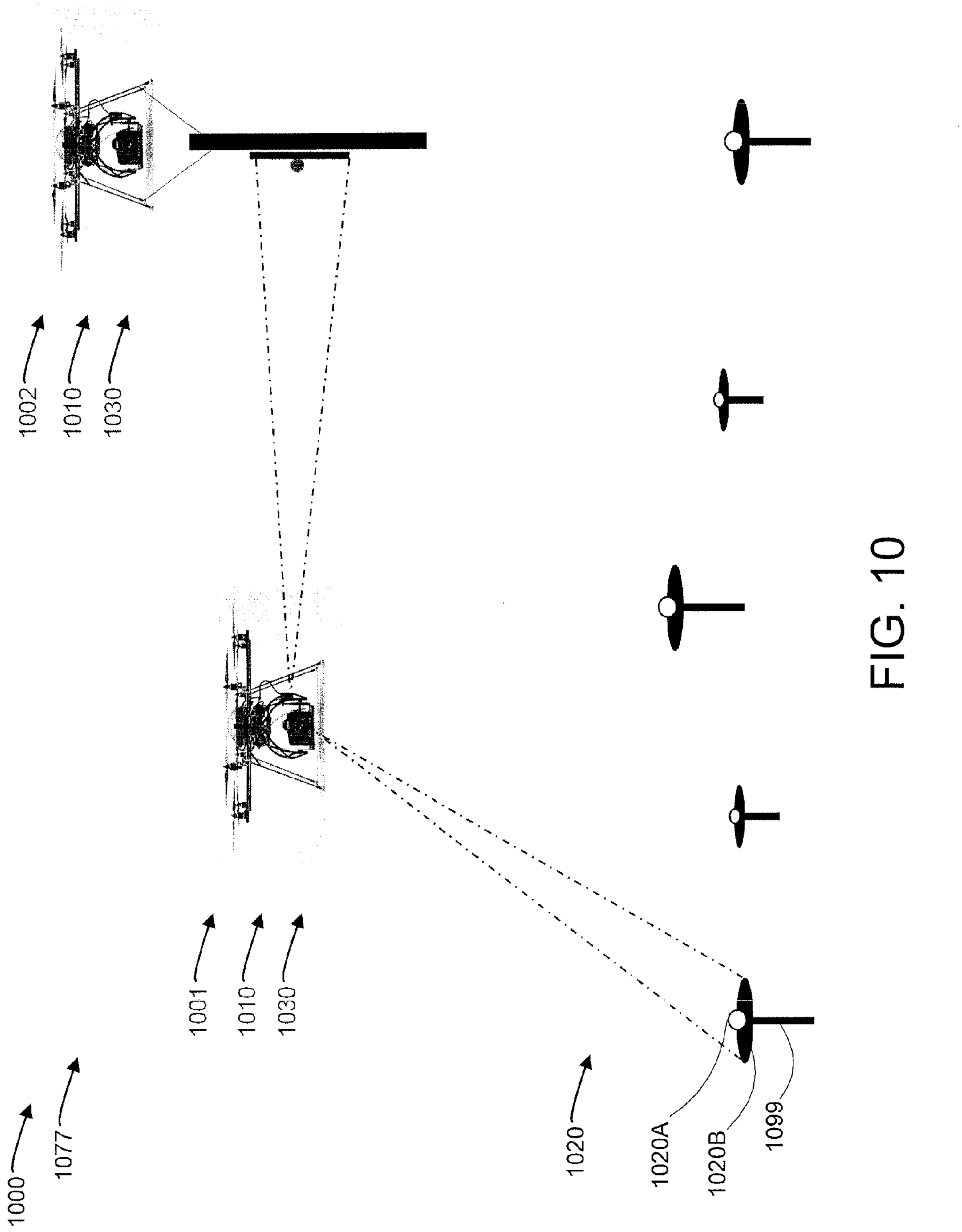
FIG. 10 shows a system 1000 for determining the size of a distribution of aerosols, deployed in an exemplary scenario 1077, in accordance with an embodiment of the present principles.

FIG. 10 shows a system 1000 for determining the size of a distribution of aerosols, deployed in an exemplary scenario 1077, in accordance with an embodiment of the present principles. In scenario 1077, two aeronautical vehicles 1001 and 1002 each include a hyperspectral camera 1010 for capturing hyperspectral images from a laser diode array 1020. The laser array 1020 includes pairs of laser diodes 1020A mounted on black discs 1020B, with each pair then mounted on a pole 1099. Moreover, each of the vehicles 1001 and 1002 include a data processing system 1030 for processing the hyperspectral images. Alternatively, the data processing systems 1030 (or a single data processing system) can be located at a remote site(s).

Figure 11:
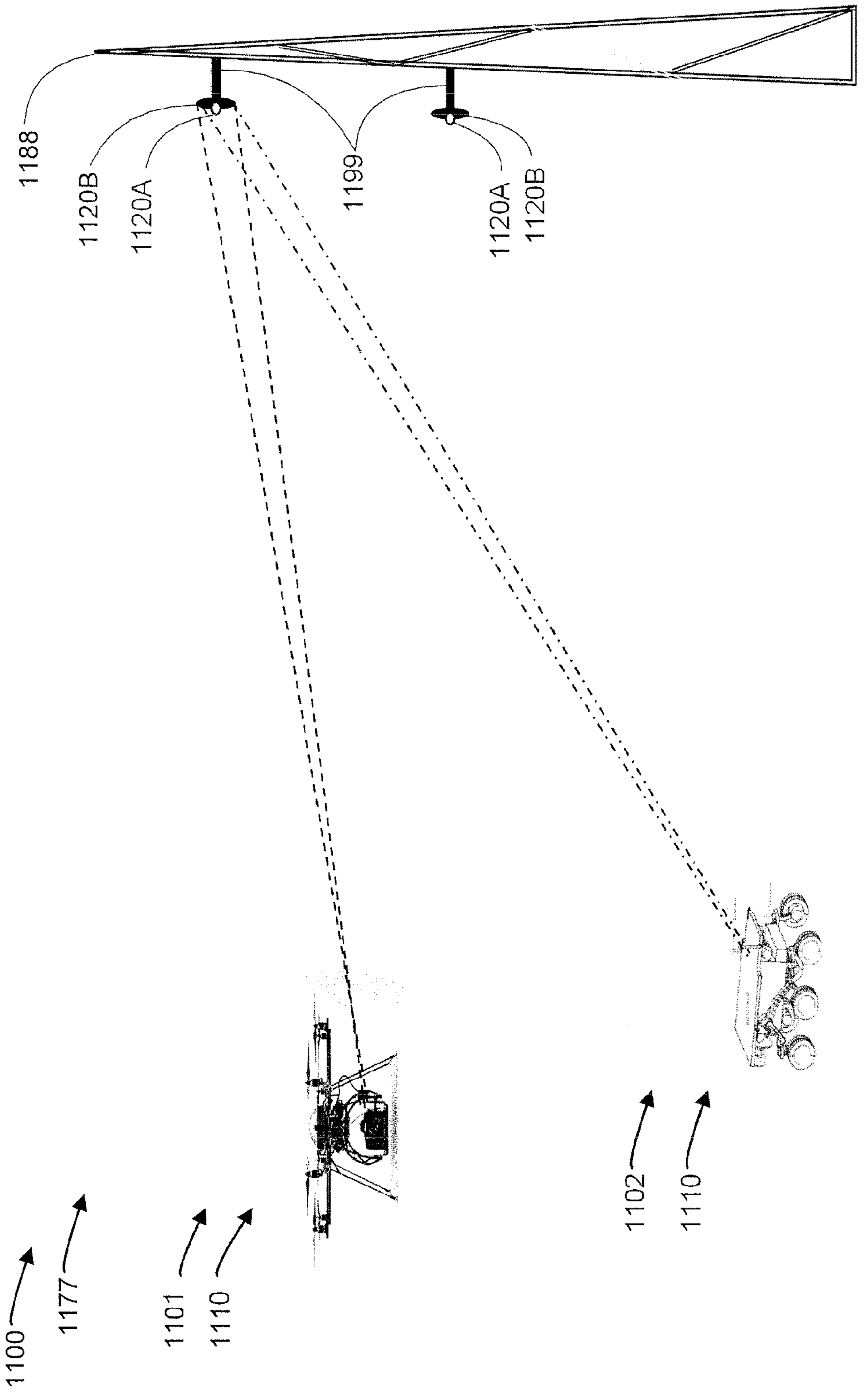
FIG. 11 shows a system 1100 for determining the size of a distribution of aerosols, deployed in an exemplary scenario 1177, in accordance with an embodiment of the present principles.

FIG. 11 shows a system 1100 for determining the size of a distribution of aerosols, deployed in an exemplary scenario 1177, in accordance with an embodiment of the present principles. In scenario 1177, two aeronautical vehicles 1101 and 1102 each include a hyperspectral camera 1110 for capturing hyperspectral images from a laser diode array 1120. The laser array 1120 includes pairs of laser diodes mounted on black discs, with each pair then mounted on a pole 1199 that is then mounted on a tower 1188. Data processing of the hyperspectral images is performed at a remote site(s). In this way, the weight of a data processing system(s) does not have be carried by the aeronautical vehicles 1101 and 1102 used to capture the hyperspectral images.

Figure 12:
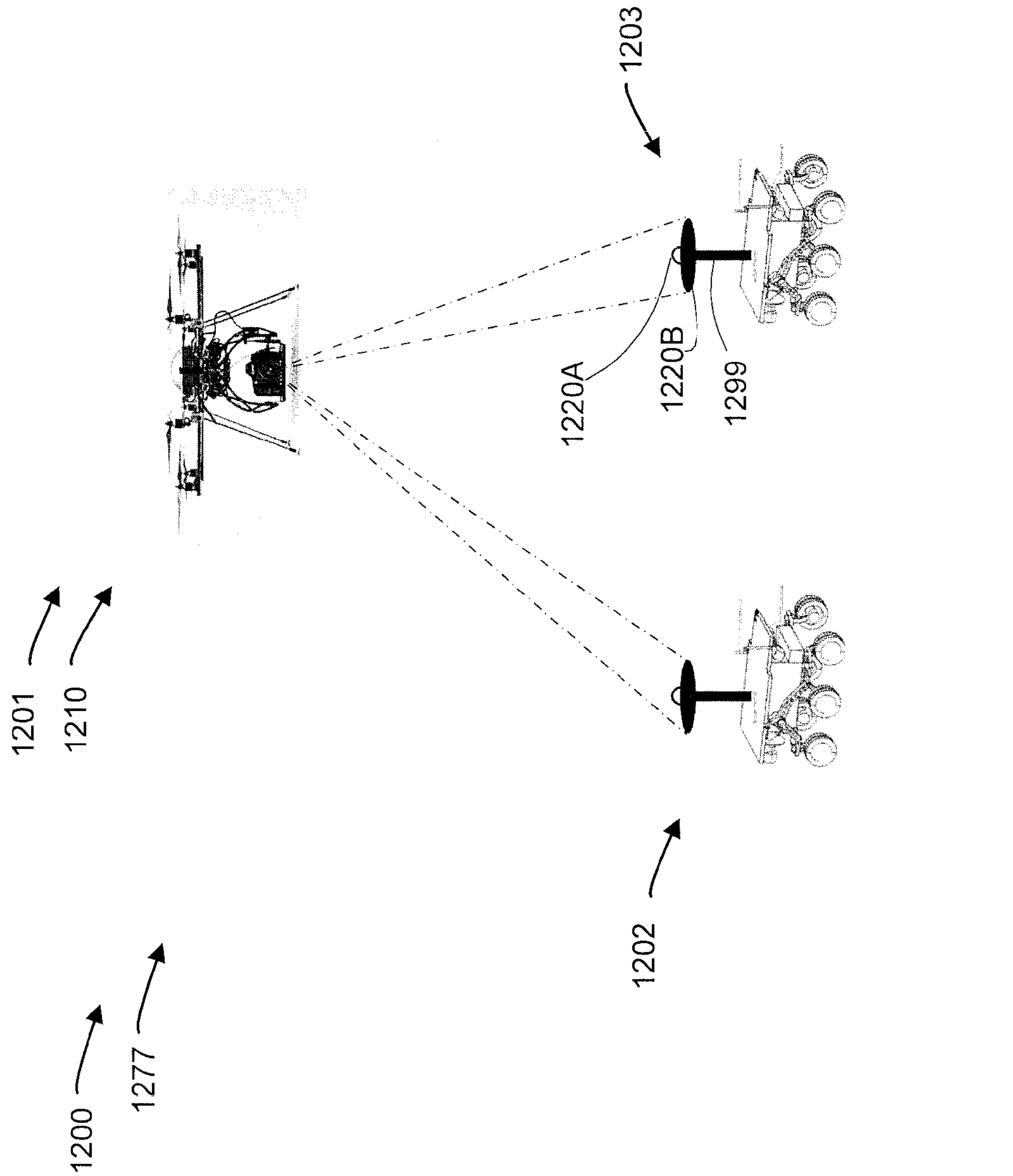
FIG. 12 shows a system 1200 for determining the size of a distribution of aerosols, deployed in an exemplary scenario 1277, in accordance with an embodiment of the present principles.

FIG. 12 shows a system 1200 for determining the size of a distribution of aerosols, deployed in an exemplary scenario 1277, in accordance with an embodiment of the present principles. In scenario 1277, aeronautical vehicle 1201 includes a hyperspectral camera 1210 for capturing hyperspectral images from a laser diode array 1220 disposed on vehicles 1202 and 1203. The laser array 1220 includes pairs of laser diodes 1220A mounted on black discs 1220B, with each pair then mounted on a pole 1299 that is then mounted on one of the vehicles 1202 and 1203. Data processing of the hyperspectral images is performed at a remote site(s). In this way, the weight of a data processing system(s) does not have be carried by the aeronautical vehicle 1001 used to capture the hyperspectral images.

The mobile source can be a calibration platform where wide angle imaging of a large surface is calibrated based on a pixel that is generated by the diode that is mounted on the vehicle. The mobile vehicle can be positioned or moving across a large area, like a city to create snapshot of images, that are stitched together to create a map of the aerosol distribution across the city. These measurement can be performed multiple times per days to capture the temporal variations of the aerosols and particulates in the city. The flying imaging system can also identify the source of pollution based on the density distribution and dispersion of the plumes. It is expected that at the source, the particles will have a wider distribution in size and be farther apart, and the smaller size particles will be more prevalent as the larger ones will settle.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. An aerosol distribution determining system, comprising:

a set of light emitters for emitting electromagnetic radiation;

a hyperspectral imaging camera for capturing hyperspectral images of the electromagnetic radiation in an absence of and in a presence of an aerosol distribution;

a data processing system for determining at least one of a size, a vertical density distribution, and a shape of particles in the aerosol distribution based on a spectral response, an angular distribution, and a polarization of the aerosol distribution derived using the hyperspectral images; and a set of black disks for absorbing at least a portion of the electromagnetic radiation emitted from the set of light emitters, wherein each of the light emitters in the set is mounted on a respective one of the black disks.

2. The aerosol distribution determining system of claim 1, further comprising a spectral response library formed from the hyperspectral images and defining a plurality of spectral responses, each of the plurality of spectral responses corresponding to an exposure of any of the black disks to a respective one of a plurality of different reference aerosol distributions.

3. The aerosol distribution determining system of claim 1, wherein the data processing system uses each of the black disks as a reference point with respect to the hyperspectral imaging camera from which the at least one of the size, the vertical density distribution, and the angular distribution of proximate points in the aerosol distribution is determined.

4. The aerosol distribution determining system of claim 1, wherein the data processing signal subtracts a black disk response signal from a laser diode response signal, respectively corresponding to a given one of the black disks and a corresponding one of the light emitters mounted thereon, to approximate a spectral response at a point in the aerosol distribution at which the given one of the black disks and the corresponding one of the light emitters are located.

5. The aerosol distribution determining system of claim 1, wherein each of the hyperspectral images represent a respective wavelength range of the electromagnetic spectrum, and wherein the data processing system combines the hyperspectral images to form a three-dimensional $(x,y,\lambda)$ hyperspectral data cube for processing and analysis, where x and y represent two spatial dimensions of a given scene, and $\lambda$ represents a spectral dimension comprising a range of wavelengths.

6. The aerosol distribution determining system of claim 1, wherein the hyperspectral camera obtains angular recordings of a spectra of the light emitters, and the data processing system determines the angular distribution of the aerosol distribution using the angular recordings.

7. The aerosol distribution determining system of claim 1, wherein the data processing system performs an assessment of respective extinctions of the electromagnetic radiation emitted from the light emitters at, at least one of, different angles and different wavelengths.

8. The aerosol distribution determining system of claim 1, wherein the data processing system performs an assessment of respective halos around the light emitters due to scattering.

9. The aerosol distribution size determining system of claim 8, wherein the assessment comprises, at least one of, selecting pixels from at least one of the black disks and screening at least one of the light emitters.

10. The aerosol distribution determining system of claim 1, wherein the data processing system determines the at least one of the size, the vertical density distribution, and the shape of the particles in the aerosol distribution based on electromagnetic radiation scattering at different wavelengths that is determined using the hyperspectral images.

11. The aerosol distribution determining system of claim 1, further comprising a spectral response library formed from the hyperspectral images and defining a plurality of spectral responses for use in determining the spectral response of the aerosol distribution.

12. The aerosol distribution determining system of claim 1, wherein the set of light emitters form reference points in the aerosol distribution from which the data processing system extrapolates the at least one of the size, the vertical density distribution, and the shape of particles in the aerosol distribution for other points in the aerosol distribution.

13. A method for aerosol distribution determination, comprising:

emitting, by a set of light emitters, electromagnetic radiation;

capturing, by a hyperspectral imaging camera, hyperspectral images of the electromagnetic radiation in an absence of and in a presence of an aerosol distribution; and determining, by a data processing system, at least one of a size, a vertical density distribution, and a shape of particles in the aerosol distribution based on a spectral response, an angular distribution, and a polarization of the aerosol distribution derived using the hyperspectral images, wherein the method further comprises absorbing, by a set of black disks, at least a portion of the electromagnetic radiation emitted from the set of light emitters, and wherein each of the light emitters in the set is mounted on a respective one of the black disks.

14. The method of claim 13, wherein the data processing system determines the at least one of the size, the vertical density distribution, and the shape of the particles in the aerosol distribution based on electromagnetic radiation scattering at different wavelengths that is determined using the hyperspectral images.

15. The method of claim 13, further comprising forming a spectral response library from the hyperspectral images that defines a plurality of spectral responses for use in determining the spectral response of the aerosol distribution.

16. The method of claim 13, wherein the set of light emitters form reference points in the aerosol distribution from which the data processing system extrapolates the at least one of the size, the vertical density distribution, and the shape of particles in the aerosol distribution for other points in the aerosol distribution.

17. The method of claim 13, further comprising a spectral response library formed from the hyperspectral images and defining a plurality of spectral responses for use in determining the spectral response of the aerosol distribution.

18. The method of claim 13, wherein the set of light emitters form reference points in the aerosol distribution from which the data processing system extrapolates the at least one of the size, the vertical density distribution, and the shape of particles in the aerosol distribution for other points in the aerosol distribution.

19. A computer program product for aerosol distribution determination, the computer program product comprising a non-transitory computer readable storage medium having program instructions embodied therewith, the program instructions executable by a computer to cause the computer to perform a method comprising:

emitting, by a set of light emitters, electromagnetic radiation;

capturing, by a hyperspectral imaging camera, hyperspectral images of the electromagnetic radiation in an absence of and in a presence of an aerosol distribution; and determining, by a data processing system, at least one of a size, a vertical density distribution, and a shape of particles in the aerosol distribution based on a spectral response, an angular distribution, and a polarization of the aerosol distribution derived using the hyperspectral images, wherein the method further comprises absorbing, by a set of black disks, at least a portion of the electromagnetic radiation emitted from the set of light emitters, and wherein each of the light emitters in the set is mounted on a respective one of the black disks.

* * * * *